United States Patent [19]
Huber et al.

[11] Patent Number: 5,702,551
[45] Date of Patent: Dec. 30, 1997

[54] METHOD FOR ASSEMBLING A MULTI-PIECE ABSORBENT ARTICLE

[75] Inventors: Michael T. Huber; David W. Cabell, both of Cincinnati; Robert J. Jezek, Sr., Fairfield; David J. K. Goulait, Cincinnati, all of Ohio

[73] Assignee: The Procter & Gamble Company, Cincinnati, Ohio

[21] Appl. No.: 627,866

[22] Filed: Apr. 3, 1996

[51] Int. Cl.$^6$ .................................................. B32B 31/08
[52] U.S. Cl. ................. 156/73.1; 156/73.5; 156/164; 156/229; 156/265; 156/269; 156/302; 156/308.2
[58] Field of Search .................. 156/64, 73.1, 161, 156/163, 164, 229, 324, 361, 362, 73.5, 250, 256, 264, 265, 269, 299, 302, 308.2

[56] References Cited

U.S. PATENT DOCUMENTS

| | | | |
|---|---|---|---|
| 3,862,634 | 1/1975 | Small | 128/284 |
| 3,893,460 | 7/1975 | Karami | 28/287 |
| 3,897,293 | 7/1975 | Babcock | 156/227 |
| 3,963,557 | 6/1976 | Patterson | 156/519 |
| 4,144,887 | 3/1979 | Milnamow | 128/287 |
| 4,171,239 | 10/1979 | Hirsch et al. | 156/461 |
| 4,364,787 | 12/1982 | Radzins | 156/164 |
| 4,491,493 | 1/1985 | Eaton | 156/235 |
| 4,525,229 | 6/1985 | Suzuki et al. | 156/161 |
| 4,531,992 | 7/1985 | Eaton | 156/152 |
| 4,576,600 | 3/1986 | Joa | 604/390 |
| 4,692,368 | 9/1987 | Taylor et al. | 428/137 |
| 4,854,985 | 8/1989 | Soderlund et al. | 156/85 |
| 4,883,549 | 11/1989 | Frost et al. | 156/161 |
| 4,995,928 | 2/1991 | Sabee | 156/164 |
| 5,004,630 | 4/1991 | Polski | 427/208.8 |
| 5,021,111 | 6/1991 | Swenson | 156/264 |
| 5,106,384 | 4/1992 | Polski | 604/390 |
| 5,259,902 | 11/1993 | Muckenfuhs | 156/164 |
| 5,264,264 | 11/1993 | Shibata et al. | 428/40 |
| 5,288,546 | 2/1994 | Roessler et al. | 428/284 |
| 5,342,685 | 8/1994 | Gobran | 428/355 |
| 5,399,177 | 3/1995 | Blaney et al. | 604/389 |
| 5,399,219 | 3/1995 | Roessler et al. | 156/259 |
| 5,482,588 | 1/1996 | Goulait et al. | 156/264 |
| 5,487,809 | 1/1996 | Goulait et al. | 156/259 |

FOREIGN PATENT DOCUMENTS

| | | | |
|---|---|---|---|
| 4-226183 | 8/1992 | Japan . | |
| 93/22996 | 11/1993 | WIPO . | |
| WO 95-19752 | 7/1995 | WIPO | A61F 13/15 |
| WO 96/03952 | 2/1996 | WIPO | A61F 13/15 |

*Primary Examiner*—James Sells
*Attorney, Agent, or Firm*—Kevin C. Johnson; Steven W. Miller; Jacobus C. Rasser

[57] ABSTRACT

A method for assembling a multi-piece absorbent article. A chassis is fed to a first assembly station at a first velocity. An ear web is fed to a second assembly station at a second velocity which is less than the first velocity. An adhesive tape substrate is fed to the second assembly station at a third velocity which is less than the second velocity. The adhesive tape substrate is cut into individual tape tabs. The individual tape tabs are bonded to the ear web at the second assembly station. The ear web having the individual tape tabs bonded thereto is then fed to the first assembly station where it is cut into individual ear pieces which are then bonded to the chassis to form a multi-piece absorbent article.

22 Claims, 2 Drawing Sheets

METHOD FOR ASSEMBLING A MULTI-PIECE ABSORBENT ARTICLE

FIELD OF THE INVENTION

The present invention relates to a method for making disposable absorbent articles, and more particularly, to a method for assembling a multi-piece disposable absorbent article.

BACKGROUND OF THE INVENTION

Infants and other incontinent individuals wear absorbent articles such as diapers to receive and contain urine and other body exudates. Absorbent articles function both to contain the discharged materials and to isolate the wearer's garments and bed clothing. Disposable absorbent articles having many different basic designs are known to the art.

Conventional disposable diapers comprise a chassis comprising an absorbent element (also referred to as an absorbent core) interposed between a previous body-contacting element (also referred to as a topsheet) and an impervious protective barrier (also referred to as a backsheet). A fastener such as an adhesive tape tab or a mechanical fastener is used to secure the absorbent article about the waist of the wearer. Such fasteners are typically secured directly to the chassis.

Multi-piece disposable diapers like conventional disposable diapers comprise a chassis comprising a topsheet, a backsheet joined to the topsheet and an absorbent core interposed between the topsheet and backsheet. Multi-piece disposable absorbent articles, like the name implies, also comprise other components, such as ear pieces, which are joined to the chassis, to form a portion of the waist region. Fasteners are joined to the ear pieces to secure the disposable diaper about the waist of the wearer. Placing the fasteners on the ear pieces after they have been attached to the chassis can cause variation of the placement of the fastener on the ear piece and jeopardize the reliability of the bonding of the fastener to the ear piece.

The present invention provides a method for assembling a multi-piece absorbent article which substantially eliminates the variation of the placement of the fastener on the ear piece and increases the reliability of the bonding of the fastener to the ear piece.

This and other objectives of the present invention will be more readily apparent when considered in reference to the following description and when taken in conjunction with the accompanying drawings.

SUMMARY OF THE INVENTION

The present invention provides a method for assembling a multi-piece absorbent article. A chassis comprising a liquid pervious topsheet, a liquid impervious backsheet joined to the topsheet, and an absorbent core positioned between the topsheet and the backsheet is fed to a first assembly station at a first velocity, V1. An ear web is fed to a second assembly station at a second velocity, V2. The second velocity, V2, is less than the first velocity, V1. A securement member substrate is fed to the second assembly station at a third velocity, V3. The third velocity, V3, is less than said second velocity, V2. The securement member substrate is cut into individual securement members. The individual securement members are bonded to the ear web at the second assembly station. The ear web having the individual securement members bonded thereto is fed to the first assembly station at the second velocity, V2. The ear web is then cut into individual ear pieces. The individual ear pieces are then bonded to the chassis at the first assembly station to form a multi-piece absorbent article.

BRIEF DESCRIPTION OF THE DRAWINGS

While the specification concludes with claims particularly pointing out and distinctly claiming the subject matter which is regarded as the present invention, it is believed that the invention will be better understood from the following description which is taken in conjunction with the accompanying drawings, in which:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article, (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner.

Figure 1:
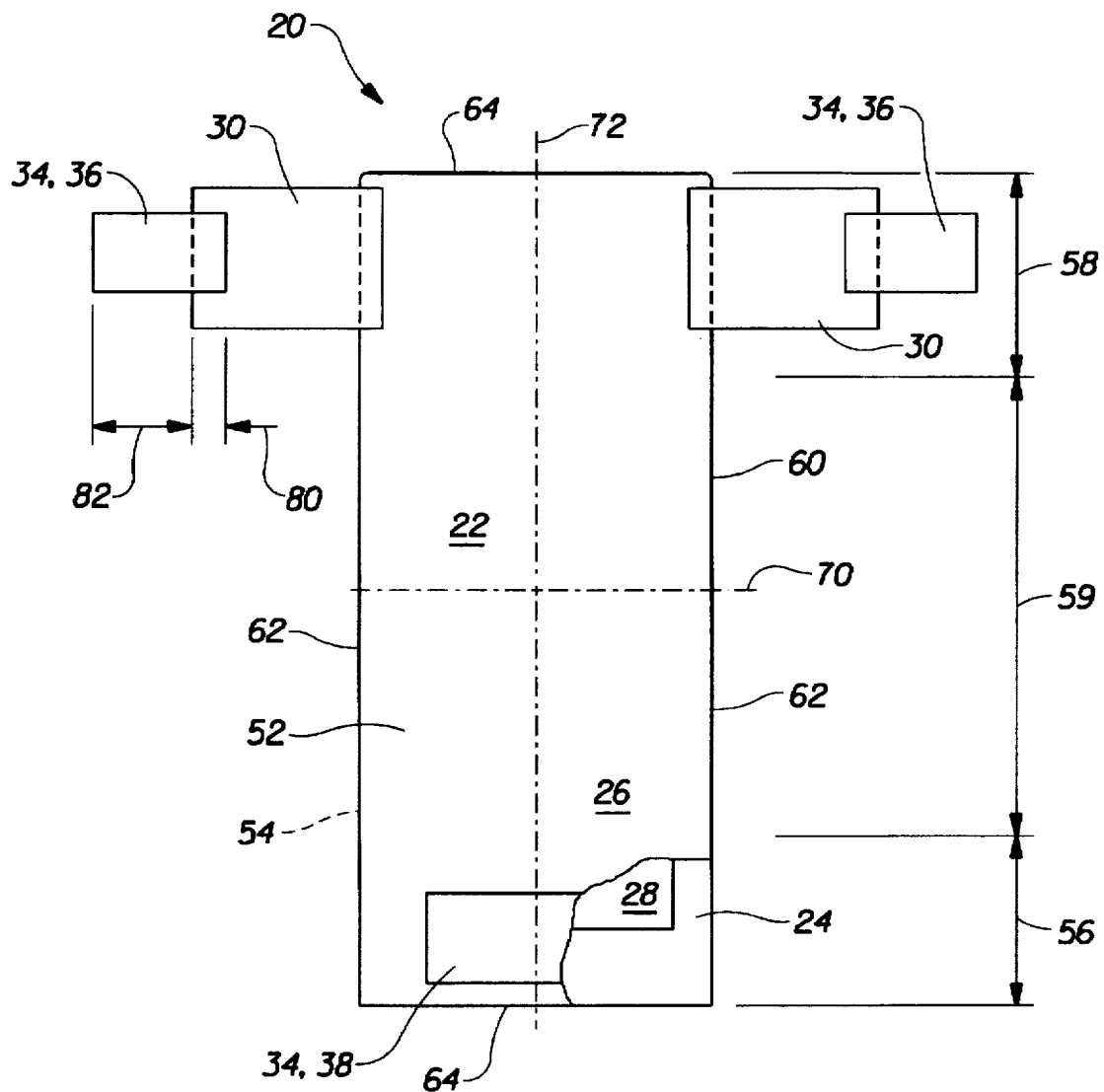
FIG. 1 is a plan view of a disposable diaper embodiment of the present invention having portions cut-away to reveal the underlying structure.

A preferred embodiment of an absorbent article of the present invention is the unitary disposable absorbent article, diaper 20, shown in FIG. 1. As used herein, the s term "diaper" refers to an absorbent article generally worn by infants and incontinent persons that is worn about the lower torso of the wearer. It should be understood, however, that the present invention is also applicable to other absorbent articles such as incontinence briefs, incontinence undergarments, feminine hygiene garments, and the like.

FIG. 1 is a plan view of the diaper 20 of the present invention in its flat-out, uncontracted state (i.e., with all elastic induced contraction pulled out) with portions of the structure being cut-away to more clearly show the construction of the diaper 20 and with the portion of the diaper 20 which faces away from the wearer, the outer surface 52, facing the viewer. As shown in FIG. 1, the diaper 20 comprises a containment assembly or chassis 22 preferably comprising a liquid pervious topsheet 24, a liquid impervious backsheet 26 joined with the topsheet 24, and an absorbent core 28 positioned between the topsheet 24 and the backsheet 26. The diaper 20 preferably further comprises individual ear pieces 30 and a fastening system 34 comprising a pair of securement members 36 and a landing member 38.

The diaper 20 is shown in FIG. 1 to have an outer surface 52 (facing the viewer in FIG. 1), an inner surface 54 opposed to the outer surface 52, a front waist region 56, a back waist region 58, a crotch region 59 positioned between the front waist region 56 and the back waist region 58, and a periphery 60 which is defined by the outer edges of the diaper in which the longitudinal edges are designated 62 and the end edges are designated 64. The diaper 20 additionally has a lateral or transverse centerline which is designated 70 and a longitudinal centerline designated 72 which is perpendicular to the lateral centerline 70. An example of a preferred absorbent article of the present invention is more fully and completely described in International Publication Number We 95/22951, The Procter & Gamble Company, published Aug. 31, 1995 in the name of Roe, et at., which is hereby incorporated by reference herein.

Figure 2:
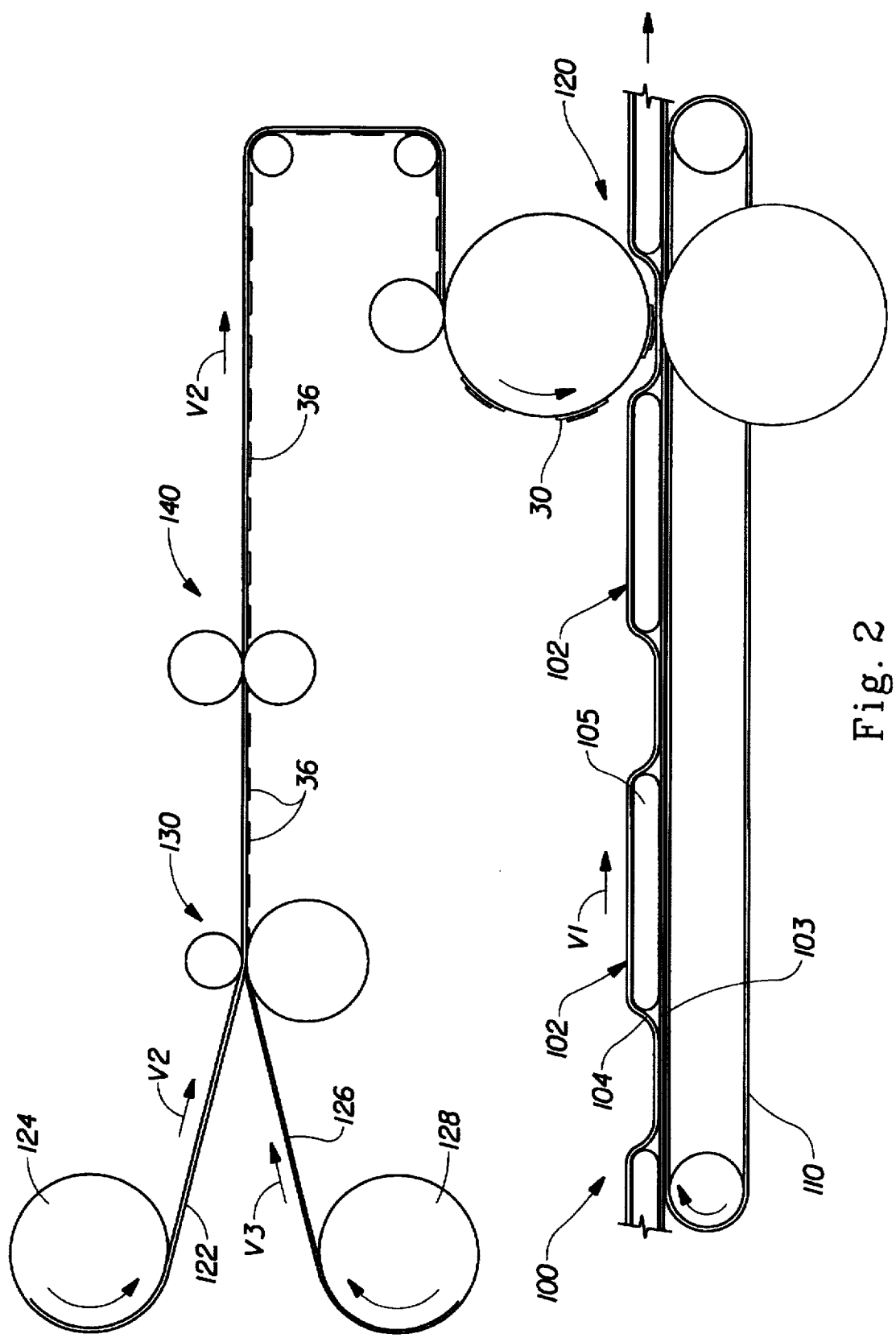
FIG. 2 is a simplified side elevation view showing the method for assembling a multi-piece absorbent article of the present invention.

Referring now to FIG. 2 there is shown a simplified side elevation view showing the method for assembling the multi-piece disposable diaper of the present invention. A continuous web 100 comprised of a plurality of interconnected chassises 102 are fed on conveyer 110 to first assembly station 120. Each chassis 102 comprises a liquid pervious topsheet 103, a liquid impervious backsheet 104 and an absorbent core 105. The continuous web 100 comprised of a plurality of interconnected chassises 102 is fed to the first assembly station 120 at a first velocity V1. First velocity, V1, is preferably from about 300 to about 1,200 feet per minute.

An ear web 122 is unwound from supply roll 124 and fed to a second assembly station 130. The ear web 122 is fed to the second assembly station 130 at a second velocity, V2. Second velocity V2 is less than the first velocity V1. Preferably, the second velocity, V2, is from about 50 to about 250 feet per minute. Ear web 122 preferably comprises a laminate comprising a nonwoven web and a polymeric film. Other suitable materials for the ear web 122 include, but are not limited to nonwoven webs, polymeric films, elastomeric nonwovens, elastomeric films, elastomeric scrim, elastomeric foam, and the like. In the embodiment shown in FIG. 2, only a single ear web is fed to the second assembly station 130. However, it may be desirable to feed a pair of ear webs to the second assembly station in order to provide an ear piece on either side of the chassis 22.

A securement member substrate 126 is unwound from supply roll 128 and is fed to the second assembly station 130. The securement member substrate is fed to the second assembly station 130 at a third velocity, V3. The third velocity V3 is preferably from about 20 to about 150 feet per minute.

It is important that the second velocity, V2, (the velocity of the ear web), be less than the first velocity, V1, (the velocity of the chassis), and that the third velocity, V3, (the velocity of the securement member substrate), be less than the second velocity, V2. This will enable the securement member substrate to be cut into individual securement members and secured to the ear web in the appropriate position and then allow the ear web to be cut into individual ear pieces 30 and secured to the chassis in the appropriate position.

At the second assembly station 130, the securement member substrate 126 is cut into individual securement members which are then bonded to the ear web 122. The securement member substrate 126 may comprise any securement member substrate known in the art. Examples of suitable substrates include adhesive tape substrates, mechanical fastener substrates, combination mechanical and adhesive fastener substrates, and the like. After the securement member substrate 126 has been cut into individual securement members 36 such as individual adhesive tape tabs, the individual adhesive tape tabs may be bonded to the ear web using any suitable method. Examples of suitable methods for bonding the individual securement members to the ear web include but are not limited to adhesive bonding, cohesive bonding, ultrasonic bonding, heat bonding, pressure bonding, friction bonding, autogenous bonding or combinations of bonding methods. In a preferred embodiment, a pair of securement member substrates are fed to the second assembly station 130 and are cut into individual securement members and secured to either side is of the ear web 122. The ear web having the individual securement members bonded thereto is then slit into two ear webs at slitter 140 to provide an ear piece on either side of the chassis.

Referring again to FIG. 1, the diaper 20 is shown to comprise a pair of securement members 36, such as adhesive tape tabs secured to the individual ear pieces 30. The securement members 36 each comprise a fixed end 80 and a refastenable end 82. The fixed end 80 is the portion of the tape tab which is bonded to the ear piece 30 during manufacture. The refastenable end 82 is the portion of the tape tab which extends laterally outwardly beyond the edge of the ear piece 30 and that is grasped by the diaperer in securing the diaper on the wearer. The fixed end may be secured to either the outer surface of the ear piece or the inner surface of the ear piece.

Referring now to FIG. 2, the ear webs having the individual securement members bonded thereto are then fed to the first assembly station 120 at the second velocity, V2. At the first assembly station 120 the ear web having the securement members bonded thereto is cut into individual ear pieces 30. The individual ear pieces 30 are then bonded to the chassis at the first assembly station 120 to form multi-piece absorbent articles. The individual ear pieces 30 may be bonded to the chassis using any suitable method. Examples of suitable methods for bonding the individual ear pieces 30 to the chassis include but are not limited to adhesive bonding, cohesive bonding, ultrasonic bonding, heat bonding, pressure bonding, friction bonding, autogenous bonding or combinations of bonding methods. The individual ear pieces 30 may be bonded to the backsheet, the topsheet or both. The individual ear pieces 30 may also be inserted between the topsheet and backsheet and bonded to both. In a preferred embodiment, the individual ear pieces 30 are bonded directly to the backsheet. The web 100 of interconnected chassises 102 having the ear pieces bonded thereto is then cut into individual multi-piece disposable diapers. The web 100 of interconnected chassises 102 having the ear pieces bonded thereto may be cut into individual multi-piece disposable diapers at the first assembly station 120.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for assembling a multi-piece absorbent article, said method comprising the steps of:
   (a) feeding a chassis to a first assembly station at a first velocity, V1, said chassis comprising a topsheet, a backsheet joined to said topsheet, and an absorbent core positioned between said topsheet and said backsheet;
   (b) feeding an ear web to a second assembly station at a second velocity, V2, said second velocity, V2, being less than said first velocity, V1;
   (c) feeding a securement member substrate to said second assembly station at a third velocity, V3, said third velocity, V3, being less than said second velocity, V2;

(d) cutting said securement member substrate into individual securement members;

(e) bonding said individual securement members to said ear web at said second assembly station;

(f) cutting said ear web into individual ear pieces; and (g) bonding said individual ear pieces to said chassis at said first assembly station to form a multi-piece absorbent article.

2. The method of claim 1 wherein a pair of securement member substrates are fed to said second assembly station.

3. The method of claim 1 wherein a pair of ear webs are fed to said second assembly station.

4. The method of claim 1 further comprising the step of slitting said ear web to form a pair of ear webs.

5. The method of claim 1 wherein said ear web comprises a laminate.

6. The method of claim 5 wherein said laminate comprises a nonwoven web and a polymeric film.

7. The method of claim 1 wherein said individual securement members have a fixed end and a refastenable end.

8. The method of claim 7 wherein said fixed end of said individual securement members are bonded to said ear web.

9. The method of claim 1 wherein said individual securement members comprise adhesive tape tabs.

10. The method of claim 1 wherein said individual ear pieces are bonded to said backsheet.

11. The method of claim 1 wherein said individual ear pieces are bonded to said topsheet.

12. The method of claim 1 wherein said individual ear pieces are bonded between the topsheet and the backsheet.

13. The method of claim 1 wherein the step of bonding said individual securement members to said ear web comprises a bonding method selected from the group consisting of adhesive bonding, cohesive bonding, ultrasonic bonding, heat bonding, pressure bonding, friction bonding, autogenous bonding or combinations thereof.

14. The method of claim 1 wherein the step of bonding said individual ear pieces to said chassis comprises a bonding method selected from the group consisting of adhesive bonding, cohesive bonding, ultrasonic bonding, heat bonding, pressure bonding, friction bonding, autogenous bonding or combinations thereof.

15. The method of claim 1 wherein said absorbent article comprises a disposable diaper.

16. A method for assembling a multi-piece absorbent article, said method comprising the steps of:

(a) feeding a chassis to a first assembly station at a first velocity, V1, said chassis comprising a topsheet, a backsheet joined to said topsheet, and an absorbent core positioned between said topsheet and said backsheet;

(b) feeding an ear web to a second assembly station at a second velocity, V2, said second velocity, V2, being less than said first velocity, V1;

(c) feeding a securement member substrate to said second assembly station at a third velocity, V3, said third velocity, V3, being less than said second velocity, V2;

(d) cutting said securement member substrate into individual securement members;

(e) bonding said individual securement members to said ear web at said second assembly station;

(f) feeding said ear web with said individual securement members bonded thereto to said first assembly station at said second velocity, V2;

(g) cutting said ear web into individual ear pieces; and (h) bonding said individual ear pieces to said chassis at said first assembly station to form a multi-piece absorbent article.

17. The method of claim 16 wherein a pair of securement member substrates are fed to said second assembly station.

18. The method of claim 16 further comprising the step of slitting said ear web to form a pair of ear webs.

19. The method of claim 16 wherein said ear web comprises a laminate.

20. The method of claim 16 wherein said individual securement members have a fixed end and a refastenable end.

21. The method of claim 20 wherein said fixed end of said individual securement members are bonded to said ear web.

22. The method of claim 16 wherein said individual securement members comprise adhesive tape tabs.

* * * * *